United States Patent [19]

Hayashi et al.

[11] Patent Number: 4,577,976
[45] Date of Patent: Mar. 25, 1986

[54] MULTI-LAYERED THIN FILM HEAT TRANSFER GAUGE

[75] Inventors: Masanori Hayashi; Akira Sakurai; Shigeru Aso, all of Fukuoka, Japan

[73] Assignee: Kyushu University, Fukuoka, Japan

[21] Appl. No.: 662,899

[22] Filed: Oct. 19, 1984

[30] Foreign Application Priority Data

Mar. 27, 1984 [JP] Japan .................. 59-57426

[51] Int. Cl.$^4$ .......................................... G01K 17/00
[52] U.S. Cl. .......................................... 374/29; 374/30
[58] Field of Search .................................. 374/29, 30

[56] References Cited

U.S. PATENT DOCUMENTS

| 3,648,516 | 3/1972 | Paine | 374/29 |
| 3,765,238 | 10/1973 | Sumikama et al. | 374/30 |
| 4,382,154 | 5/1983 | Thery et al. | 374/30 |

FOREIGN PATENT DOCUMENTS 2758994  7/1979  Fed. Rep. of Germany ........ 374/29

OTHER PUBLICATIONS

"An Improved Thin-Film Gauge for Shock Tube Thermal Studies", Willeke, Klaus and Bershader, Daniel, The Review of Scientific Instr., vol. 44, No. 1, Jan. '73, pp. 22-25.

Primary Examiner—Charles Frankfort
Assistant Examiner—Thomas B. Will
Attorney, Agent, or Firm—Spencer & Frank

[57] ABSTRACT

A pair of metallic thin films are attached to opposite surfaces of a heat resistive thin film, and the heat flux through the heat resistive thin film is determined by measuring the temperature gradient therein while using the metallic thin films as resistance thermometer elements.

2 Claims, 22 Drawing Figures

FIG_5
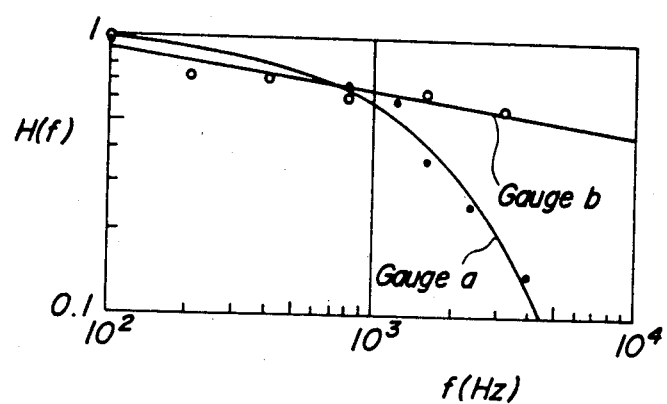
FIG_6
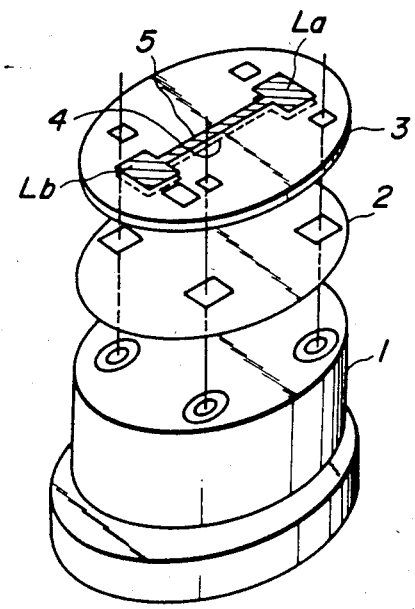

FIG_8A
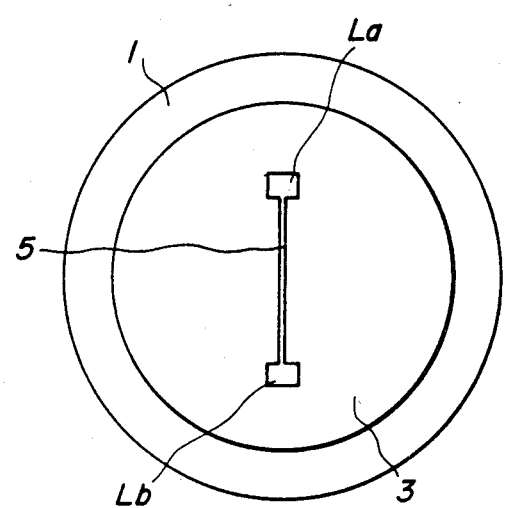
FIG_8B
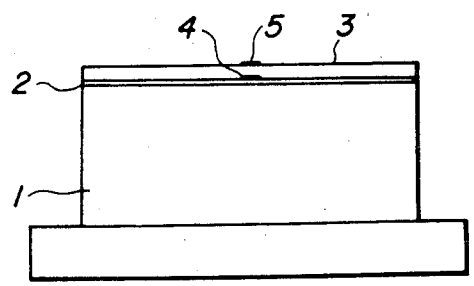

FIG.11
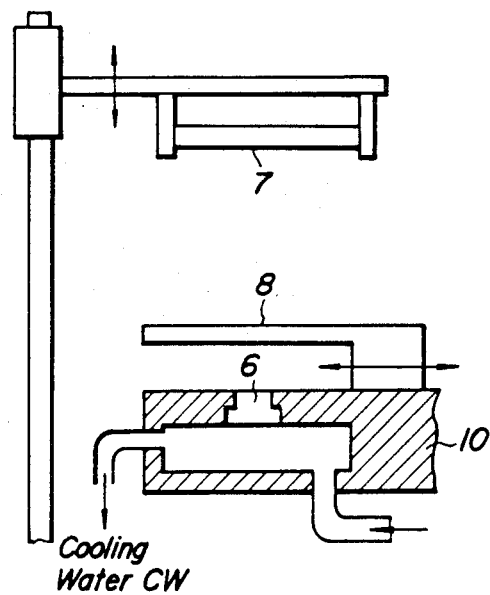
Cooling Water CW
FIG.12A 10μV
FIG.12B 40μV
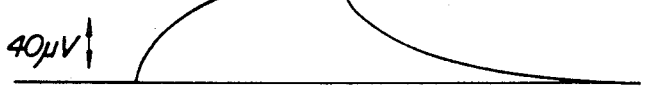
FIG.12C
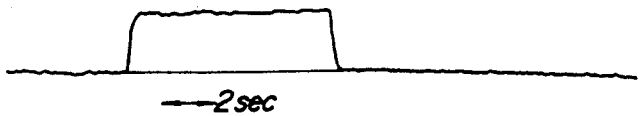
←2sec

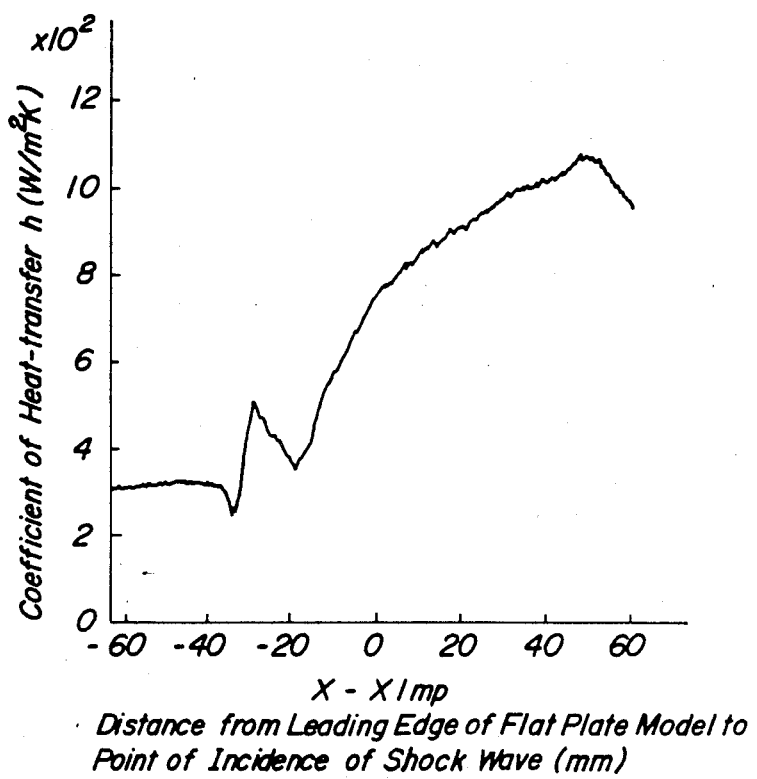
FIG_15

MULTI-LAYERED THIN FILM HEAT TRANSFER GAUGE

BACKGROUND OF THE INVENTION

1. Field of the Invention

This invention relates to a multi-layered thin film heat transfer gauge for determining heat flow into an object by measuring the temperature gradient across a thin, heat resistive film with resistance thermometers having metallic thin film elements. More particularly, the invention relates to a heat transfer gauge made of thin films overlaid one over the other and adapted to measure heat flux of long duration at high spatial resolution with quick response.

2. Description of the Prior Art

A conventional heat transmission gauge of the thin film type, for instance that which has been used fairly frequently for measurements concerning shock wave tubes, has a heat-insulating substrate made of PYREX or the like and metallic thin films deposited on the substrate so as to form a resistance thermometer. The conventional heat transfer gauge of this type measures the transient and non-steady surface temperature rise of an object caused by an input heat flux, and the heat flux at the surface of the object is determined from the thus measured temperature rise by calculation. This heat transfer gauge using thin films has been practically the only one which has a high spatial resolution and quick response.

The conventional heat transfer gauge using thin films, however, has a shortcoming in that, since its principle of measuring the heat flux is based on the transient temperature rise of the surface of a heat-insulating thermally non-conductive substrate, it is applicable only to the measurement of that heat flux which is produced in a wind tunnel with short flow duration. If such conventional heat transfer gauge is applied to the measurement of heat flux in a supersonic or low-speed wind tunnel with long flow duration, the surface temperature of the object being tested is raised quickly and the conditions of constant-temperature wall are not satisfied, so that it cannot measure the steady state heat flux which is indispensable for heat flux measurement in such wind tunnels.

Thus, the conventional heat transfer gauge of the thin film type has been considered as the only heat flux sensor having a high spatial resolution and a quick response, but it has a shortcoming in that it is applicable only to the measurement of heat flux in a shock wave tube or other wind tunnels with short flow duration, so that its scope of application is rather limited. In fact there is no heat flux sensor with a high spatial resolution and a quick response which is applicable to the measurement of heat flux in a wind tunnel with long flow duration.

On the other hand, the study of heat transfer to the surface of an object has become very important in the technical fields of aeronautical engineering, space engineering, and like, especially in the research related to supersonic flight, re-entry to atmosphere, gas flow in prime movers, etc. In the problems of the above-mentioned study, a shift of spatial position on a very minute scale results in a large change of heat flux, so that the heat flux variation in such study is very difficult to measure, if not impossible, by the conventional heat transfer gauge of the thin film type. Accordingly, the phenomenon of local heat transfer inherent to the problems of the above study have been left unclear.

Thus, another disadvantage of the conventional heat transfer gauge of the thin film type is in that it is applicable only to a comparatively narrowly limited technical field.

SUMMARY OF THE INVENTION

Therefore, an object of the present invention is to obviate the above-mentioned shortcomings of the prior art by providing an improved thin film heat transfer gauge having high spatial resolution and quick response, which gauge is capable of measuring steady state heat flux such as those in a wind tunnel with long flow duration. A thin film heat transfer gauge of the invention is applicable to the study of the phenomenon of local heat transfer in which heat flux varies greatly for a small shift of spatial position of measurement on a very fine scale. More particularly, the invention provides a multi-layered heat transfer gauge made of thin films overlaid one over another.

Another object of the invention is to provide a thin film heat transfer gauge, more particularly a multi-layered heat transfer gauge made of thin films overlaid one over another, which gauge is suitable for measurement of heat flux in various technical fields where a high spatial resolution and a quick response are required.

A further object of the invention is to provide a thin film heat transfer gauge, more particularly a multi-layered heat transfer gauge made of thin films overlaid one over another, which gauge is suitable for accurate measurement of thermal load encountered in aeronautical industry, space industry, machine industry, nuclear industry, or other industries involving heat transfer. The accurate measurement enabled by the heat transfer gauge of the invention will contribute to the improvement of the design of various machines and apparatus in those industries, such as machines and parts moving at supersonic or hypersonic speeds, turbine or other prime mover mechanisms operating at supersonic speeds, and the like.

To fulfil the above objects, an embodiment of the multi-layered heat transfer gauge of the invention uses a structure in which a pair of metallic thin films are bonded to opposite surfaces of a heat resistive thin film, the metallic thin films being connected to a resistance thermometer as elements thereof. In this way, a temperature gradient produced in the heat resistive thin film by a heat flux flowing therein is measured by the resistance thermometer connected with the metallic thin films, and this heat flux is determined directly from the thus measured temperature gradient by calculation.

BRIEF DESCRIPTION OF THE DRAWINGS

For better understanding of the invention, reference is made to the accompanying drawing, in which:

FIG. 5 is a graph showing the comparison of the frequency response characteristics of the gauge of the invention and the corresponding characteristics of the prior art. In FIG. 5, gauge a is made by a vacuum evaporation technique and gauge b by a sputtering technique;

FIG. 6 is an exploded perspective view showing an embodiment of the multi-layered heat transfer gauge of the invention in which a synthetic resin film is used as a heat resistive thin film;

FIG. 8A and FIG. 8B are a plan view and an elevation of a multi-layered structure including a heat resistive thin film made of synthetic resin, which structure is used in the heat transfer gauge of the invention;

FIG. 11 is a schematic sectional view of an apparatus for calibration of the multi-layered heat transmission gauge of the invention;

FIGS. 12A, 12B and 12C show waveforms of signals representing the sequence in which a measured value is calibrated;

FIG. 15 is a graph showing the result of a series of measurements obtained by using a multi-layered heat transfer gauge according to the invention.

Figure 1:
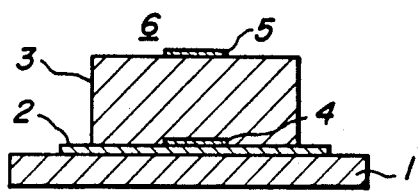
FIG. 1 is a schematic vertical sectional view of the essential structure of a multi-layered heat transfer gauge according to the present invention.

Throughout different views of the drawing, 1 is a substrate made of heat conductive material, 2 is an electric insulation layer, 3 is a heat resistive thin film, 4 and 5 are metallic thin films acting as resistance thermometer elements, 6 is a heat flux sensor, 7 is a halogen lamp, 8 is a shutter, 9 is a probe, 10 is an object being measured, $r_1$ and $r_2$ are the electric resistances of the metallic thin films and $L_a$, $L_b$ are lead wire portions, and $A_1$ and $A_2$ are D.C. amplifiers.

DESCRIPTION OF THE PREFERRED EMBODIMENTS

The invention will be described in detail by referring to preferred embodiments illustrated in the drawing.

FIG. 1 illustrates the basic structure of a multilayered heat transfer gauge according to the present invention. In the figure, a substrate 1 is made of a heat conductive material, and an electric insulation layer 2 which is thick enough to provide a required level of electric insulation is attached to the top surface of the substrate 1. A heat resistive thin film 3 carries a pair of metallic thin films 4 and 5 bonded to the opposite surfaces thereof and this heat resistive thin film 3 is attached to the top surface of the electric insulation layer 2. Thereby, a heat flux sensor 6 is formed. The metallic thin films 4 and 5 act as elements of a resistance thermometer to be described hereinafter.

The fundamental principles of the multi-layered heat transfer gauge of the invention with the above basic structure is as follows. The overall thickness of the heat flux sensor 6 having the heat resistive thin film 3 carrying the metallic thin films 4 and 5 is made very thin, and such thin heat flux sensor 6 is attached onto the surface of an object being measured while inserting the electric insulation layer 2 and the substrate 1 therebetween. The electric insulation layer 2 is so thin that it does not disturb the heat flow between the sensor 6 and the object being measured, and the substrate 1 is made of a heat conductive material. When heat flows from the object to the sensor 6 through the substrate 1 and the electric insulation layer 2, the heat flux of such heat flow produces a temperature gradient in the heat resistive thin film 3. Such temperature gradient can be measured by the metallic thin films 4 and 5 acting as resistive thermometer elements, and the heat flux through the heat resistive thin film 3 can be determined directly from the thus measured temperature gradient by calculation.

Thus, the heat flux sensor 6 according to the invention determines the heat flux through the heat resistive thin film 3 by measuring the temperature difference across the opposite surfaces of the heat resistive thin film 3 on the basis of the above-mentioned simple principle. Despite its multi-layered structure, the heat flux sensor 6 of the invention can determine the heat flux through an object or a field to be measured without disturbing the heat flow therein because the individual films constituting the multi-layered structure are very thin.

The heat flux sensor 6 of the above structure according to the invention can be made very small, as will be described hereinafter by referring to examples, yet it has a high spatial resolution and a quick response, and its measured data can be easily calibrated as will be explained hereinafter. More particularly, the multi-layered assembly in the heat flux sensor 6 of the invention comprises only the heat resistive thin film 3 carrying metallic thin films 4 and 5 bonded to the opposite surfaces thereof, and all such thin films 3, 4, and 5 can be easily produced and bonded by currently available thin film technology. In fact, the multi-layered assembly can be made by using various kinds of material in any shape with any desired dimensions so as to meet the needs of a specific application.

The method for determining the heat flux from the measured temperature difference across the heat resistive thin film 3 in the heat flux sensor 6 of the above structure of the invention will be described now by referring to FIG. 1 and FIG. 2.

If the heat conductivity and the thickness of the heat resistive thin film 3 are denoted by k and L respectively, and the temperature rises at the opposite surfaces of the thin film 3 are denoted by $T_1$ and $T_2$, then the steady state surface heat flux qw is given by the following equation (1).

$$qw = -\kappa(\partial T/\partial x)_w = \kappa \cdot (\Delta T/L); \text{ where } \Delta T = T_1 - T_2 \quad (1)$$

Here, $\Delta T$ is the temperature difference across the opposite surfaces of the heat resistive thin film 3, and such temperature difference can be indirectly determined by measuring the resistances $r_1$ and $r_2$ of the metallic thin films 5 and 4 between terminal lead portions $L_a$ and $L_b$ (see FIG. 3), which metallic thin films 4 and 5 are bonded to the opposite surfaces of the heat resistive thin film 3.

Figure 2:
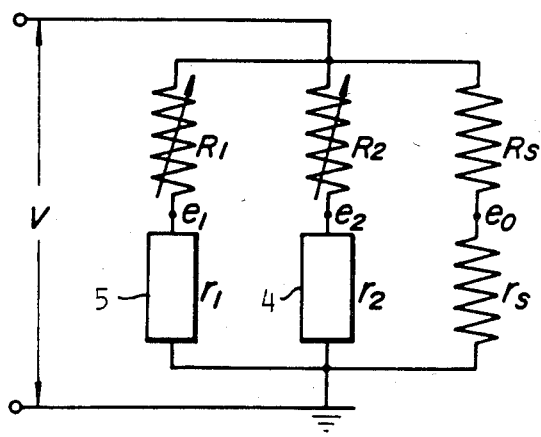
FIG. 2 is a schematic circuit diagram of an example of a bridge circuit to be used together with the gauge of FIG. 1 for determining the measured value.

The resistances $r_1$ and $r_2$ of the metallic thin films 4 and 5 are measured by the bridge circuit of FIG. 2. If the resistances $r_1$ and $r_2$ of the metallic thin films 4 and 5 at the temperature at which the bridge circuit is balanced are denoted by $r_{10}$ and $r_{20}$, and the temperature coefficients of their resistances are denoted by $a_1$ and $a_2$, then their resistances $r_1$ and $r_2$ corresponding to the temperature rises $T_1$ and $T_2$ are given by $$\left. \begin{array}{l} r_1 = r_{10}(1 + a_1 T_1) \\ r_2 = r_{20}(1 + a_2 T_2) \end{array} \right\} \quad (2)$$

The output from the bridge circuit of FIG. 2 is given by the following equations (3) and (4).

$$\frac{e_1 - e_2}{V} = \frac{m(a_1 T_1 - a_2 T_2)}{(m+1)^2[1+\{a_1 T_1/(m+1)\}][1+\{a_2 T_1/(m+2)\}]} \quad (3)$$

$$\frac{e_2 - e_0}{V} = \frac{m a_2 T_2}{(m+1)^2[1+\{a_2 T_2/(m+1)\}]} \quad (4)$$

Here, $e_0$ is a constant voltage denoted in FIG. 2 and $m = R_s/r_s$. If one solves equation (3) for the temperature difference $\Delta T$ while neglecting the higher order term therein, it is given by the following equation (5).

$$\Delta T = \frac{(m+1)^2}{m} \cdot \frac{1}{a_1} \cdot \frac{e_1 - e_2}{V} - \frac{a_1 - a_2}{a_1} \cdot T_2 \quad (5)$$

In general, the temperature of the metallic films 4 and 5 and hence the average of the temperature rises $T_1$ and $T_2$ at the opposite surfaces of the heat resistive thin film 3 vary over a fairly wide range even though the speed of such variation is slower than that of the change in the temperature difference across the heat resistive thin film 3. Besides, the temperature coefficients $a_1$ and $a_2$ of the resistances of the metallic thin films 5 and 4 are different from each other in general. Thus, the correction as shown by the second term of equation (5) is necessary. If equations (3) and (4) are inserted in equation (5) while neglecting their higher order terms, the heat flux qw can be finally given by the following equation (6) after rearrangement.

$$qw = \gamma(\epsilon_{12} + \delta \cdot \epsilon_{20}), \epsilon_{12} = (e_1 - e_2)/V, \epsilon_{20} = (e_2 - e_0)/V \quad (6)$$

Here, $$\gamma = (\kappa/L) \cdot (1/a_1) \cdot (m+1)^2/m, \delta = (a_2 - a_1)/a_2 \quad (7)$$

Accordingly, to determine the heat flux qw, the calibration coefficients $\gamma$ and $\delta$ for the heat flux sensor 6 are calculated beforehand, and the bridge circuit outputs $(e_1 - e_2)$ and $(e_2 - e_0)$ are measured by using the heat flux sensor 6. Then, the heat flux qw is calculated from the thus measured bridge circuit outputs by using equation (6).

Actual materials and formation of the multi-layered heat transfer gauge of the invention as explained above by referring to FIG. 1 and FIG. 2 are, for instance, as follows.

(a) A heat flux sensor 6 comprising a heat resistive thin film 3 made of silicon monoxide and metallic thin films 4 and 5 in the form of nickel layers deposited on the opposite surfaces of the heat resistive thin film 3 by vacuum evaporation, the metallic thin films 4 and 5 acting as resistance thermometer elements.

(b) A heat flux sensor 6 comprising a heat resistive thin film 3 made of silicon monoxide and metallic thin films 4 and 5 in the form of nickel layers deposited on the opposite surfaces of the heat resistive thin film 3 by sputtering, the metallic thin films 4 and 5 acting as resistance thermometer elements.

(c) A heat flux sensor 6 comprising a heat resistive thin film 3 made of a polyester film and metallic thin films 4 and 5 in the form of nickel layers deposited on the opposite surfaces of the heat resistive thin film 3 by vacuum evaporation, the metallic thin films 4 and 5 acting as resistance thermometer elements.

Practical examples of the above structures tested by the inventors will be described now together with methods for making them.

Figure 3:
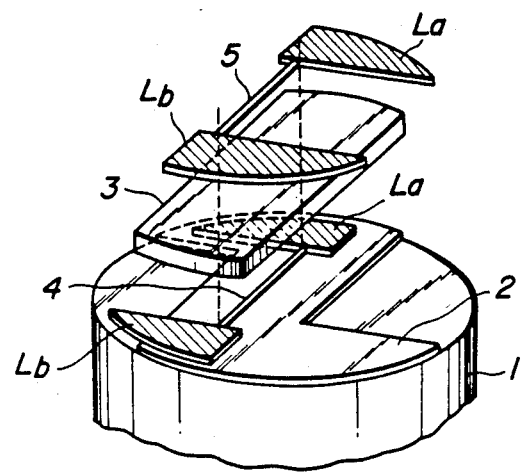
FIG. 3 is an exploded perspective view showing the manner in which a multi-layered structure to be used in the heat transfer gauge of the invention is formed by vacuum evaporation.
Figure 4:
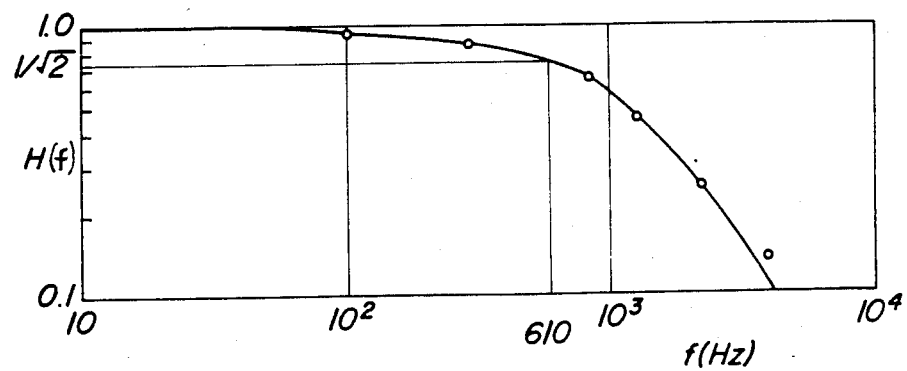
FIG. 4 is a graph showing the frequency response characteristics of a multi-layered heat transfer gauge using the structure of FIG. 3.

(a) A heat flux sensor 6 as shown in a schematic exploded view of FIG. 3 was prepared, in which the heat resistive thin film 3 was made of silicon monoxide and the metallic thin films 4 and 5 acting as resistance thermometer elements were made by vacuum evaporation of nickel. The sensor 6 included a heat conductive substrate 1 having a disk shape with a diameter of 12 mm. Each of the metallic thin films 4 and 5 had a width of 0.2 mm and a length of 3 mm. The electric insulation layer 2 of this example was also made of silicon monoxide. A thin protective layer (not shown) made of silicon monoxide was overlaid on the top surface of the upper metallic thin film 5, so as to protect it against damage due to dust particles. The thickness of the heat resistive thin film 3 was about 10 $\mu$m. The heat flux sensor 6 of FIG. 3 had a flat frequency response characteristics up to about 610 Hz as shown in FIG. 4. The measuring performance of this heat flux sensor 6 will be described hereinafter by referring to FIG. 14 and FIG. 15. (b) Another heat flux sensor 6 similar to that described in the preceding paragraph (a) was prepared by forming the nickel thin films 4 and 5 on a heat resistive silicon dioxide thin film 3 by sputtering. The width of each nickel thin film 4, 5 was 0.3 mm, and the thickness of the heat resistive silicon dioxide thin film 3 was 4 $\mu$m. Otherwise, the shape and the dimension of this heat flux sensor 6 were the same as the flux sensor described in the preceding paragraph (a) and shown in FIG. 3. Since the sputtering of the nickel thin films 4 and 5 allows the use of a very thin heat resistive thin film 3, the frequency response characteristics of the heat flux sensor using this very thin heat resistive film 3, which is shown in FIG. 5, is improved over that of the preceding example by a factor of several times, as can be seen from comparison of FIG. 5 and FIG. 4.

(c) Another heat flux sensor 6 was made by using a heat resistive thin film 3 made of polyester and nickel thin films 4, 5 acting as resistance thermometer elements deposited on the polyester thin film 3 by vacuum evaporation, as shown in the schematic exploded view of FIG. 6. Each of the nickel thin films 4 and 5 had a width of 0.1 mm and a length of 6 mm. Other dimensions of the parts of this example were similar to those of the preceding examples. Since the heat resistive thin film 3 of this example is made of a synthetic resin film, it has an advantage of being easily mountable on any curved surfaces.

Figure 7A:
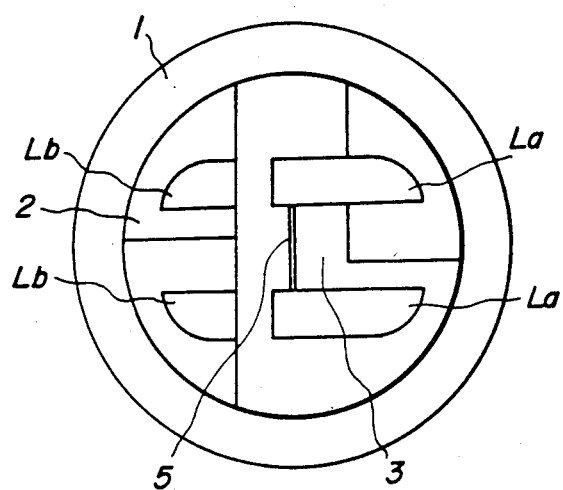
FIG. 7A and FIG. 7B are a plan view and an elevation of a multi-layered structure formed by vacuum evaporation or sputtering for use in the gauge of the invention.
Figure 7B:
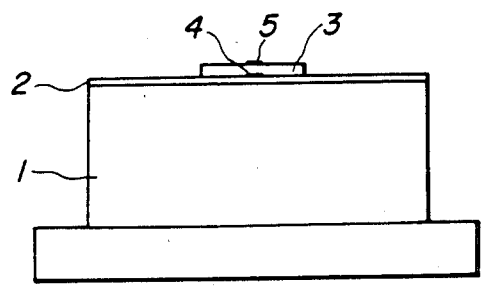

FIG. 7A and FIG. 7B show a plan view and an elevation of the heat flux sensor of FIG. 3, while FIG. 8A and FIG. 8B show a plan view and an elevation of the heat flux sensor of FIG. 6.

In the examples described above, the heat resistive thin film 3 was made of silicon monoxide, silicon dioxide or polyester, but such heat resistive thin film 3 can be made of ceramics or other suitable heat resistive material. The shape and the dimension of the heat resistive thin film 3 can be selected at will so as to meet the needs of a specific application. The material of the metallic thin films 4, 5 acting as resistance thermometer elements was nickel in the example mainly from the standpoint of economy, but it is also possible to make them with platinum so as to expand the temperature range for measurement. The shape and the dimensions of the metallic thin films 4, 5 can also be selected at will.

The performance of the multi-layered heat transfer gauge having the above structure according to the invention will now be described. As demonstrated above by referring to the heat flux sensor embodying the invention, the multi-layered heat transfer gauge can be made in a miniature size because of its simple structure comprising a heat resistive thin film 3 carrying metallic thin films 4, 5 deposited thereon so as to act as resistance thermometer elements. Accordingly, the multi-layered heat transfer gauge of the invention can measure the heat flux at a high spatial resolution with quick response, so that measurement by the gauge of the invention can accurately follow rapid changes in heat flux. The operating principle based on the steady state temperature gradient in the heat resistive thin film 3 renders a good steady state response to the gauge of the invention, which steady state response has not been available in the thin film type heat transfer gauge of the prior art.

Figure 9A:
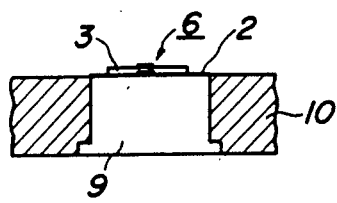
FIG. 9A, FIG. 9B, and FIG. 9C are schematic sectional views showing three different ways for mounting the multi-layered heat transfer gauge of the invention onto an object to be measured.

Referring to FIG. 9A, for practical application, a multi-layered heat transfer gauge of the invention in the form of a heat flux sensor 6 is mounted on the top surface of a probe 9, which probe is formed as an integral part of an object 10 being measured by using the same material as that of the object 10. In this case, the probe 9 acts as the substrate 1 of the heat flux sensor 6.

Figure 9C:
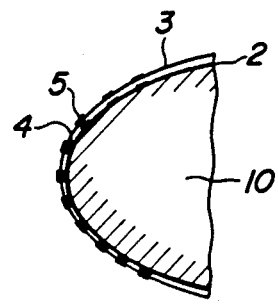
Figure 9B:
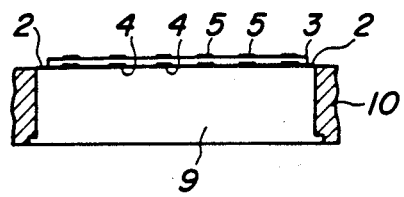

Alternatively, as shown in FIG. 9B, a number of highly sensitive heat flux sensors 6 are formed by depositing a number of paired metallic thin films 4 and 5 acting as resistance thermometer elements on opposite surfaces of a fairly large heat resistive thin film 3 at uniform intervals over the entire span of the film 3. The heat flux sensors 6 thus formed are attached to the top surface of the probe 9, so as to mount the sensors 6 on the object 10. In the case of FIG. 9C, a number of flexible heat flux sensors 6 are formed by depositing a number of paired metallic thin films 4 and 5 on opposite surfaces of a large flexible heat resistive thin film 3 at uniform intervals over the entire span of the film 3, and the thus formed sensors 6 are attached to a curved surface of the object 10 in tight contact therewith.

Figure 10:
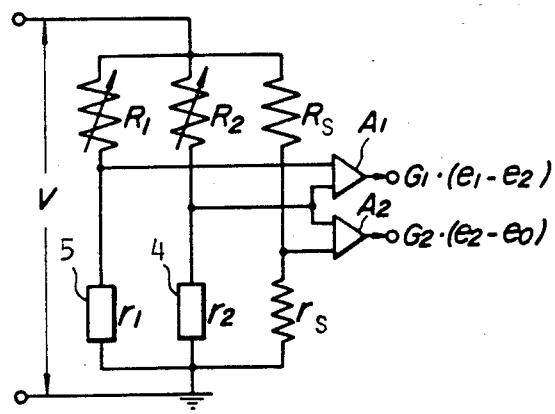
FIG. 10 shows a bridge circuit means to be used with the multi-layered heat transfer gauge of the invention for determining the measured value thereof.

To determine the heat flux at the surface of the object 10 by the thus mounted sensors 6 or the multi-layered heat transfer gauges of the invention, the paired metallic thin films 4 and 5 are connected with a bridge circuit as shown in FIG. 10, so as to provide arm resistances of the bridge circuit. The bridge circuit of FIG. 10 measures the variation of the resistance values of the metallic thin films 4 and 5 as described above by referring to FIG. 2. The heat flux can be determined from the output of the bridge circuit in the form of the equations (3) and (4) through the calculation of the equation (6). The bridge circuit output levels $(e_1-e_2)$ and $(e_2-e_0)$ given by the equations (3) and (4) may be amplified by D.C. amplifiers $A_1$ and $A_2$ with gains $G_1$ and $G_2$, and the thus amplified output levels $G_1(e_1-e_2)$ and $G_2(e_2-e_0)$ may be converted into digital signals so that heat flux is calculated by equation (6) with constants set therein, or may be input to an analogue circuit so that heat flux is obtained as an output.

The calibration constants or coefficients used in the processing of the above output from the bridge circuit and the calculation in accordance with the equation (6) must be determined beforehand. One of various methods for determining such calibration constants will be described now. In the heat transfer gauge of the invention, the two constants $\gamma$ and $\delta$ of equation (7) can be determined separately. More particularly, the coefficient $\delta$ can be determined as follows; namely, when a constant heat flux is applied to the heat transfer gauge of the invention, even if the differential voltage ratios $\epsilon_{12}$ and $\epsilon_{20}$ of the equation (6) vary in a non-steady manner, the finally obtained quantity $(\epsilon_{12}+\gamma\cdot\epsilon_{20})$ must be constant, and this condition facilitates the determination of $\delta$. The coefficient $\gamma$ can be determined as follows; namely, after the above differential voltage ratios $\epsilon_{12}$ and $\epsilon_{20}$ are stabilized at constant levels, the quantity $(\epsilon_{12}+\epsilon_{20})$ is calculated by using the coefficient $\delta$ as determined above, and the coefficient $\gamma$ can be determined from the thus calculated quantity by using the equation (6).

An example of the configuration of the calibrating means for determining the coefficient $\delta$ in the above-mentioned manner will be described now by referring to FIG. 11. In the calibrating means of FIG. 11, a halogen lamp 7 is held in a vertically slidable manner. After the halogen lamp 7 is fully heated, a shutter 8 is opened for irradiating a heat flux sensor 6 mounted on an object 10, so that heat flux is applied to the heat flux sensor 6 and non-steady output levels $\epsilon_{12}$ and $\epsilon_{20}$ are produced from which the coefficient $\delta$ is determined in the manner described above. Cooling water CW is forced through the inside of the object 10, so that the surface temperature of the sensor is not raised too much by the halogen lamp 7.

The curves of FIGS. 12A, 12B, and 12C show the non-steady output levels $\epsilon_{12}$ and $\epsilon_{20}$ obtained in the above manner and the output level obtained after calibration effected by the coefficient $\delta$ derived in the above fashion. The curves of FIGS. 12A, 12B and 12C indicate that the sensor output level $(\epsilon_{12}+\delta\cdot\epsilon_{20})$ becomes constant after the above calibration.

Figure 13A:
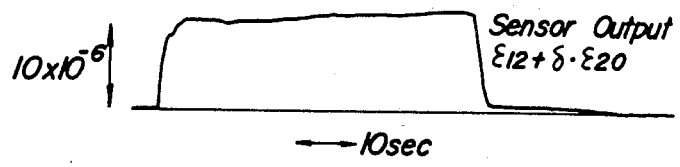
FIGS. 13A and 13B show, in a comparative manner, the result of calibration of measured values obtained by a gauge of the present invention and the result of measurement by a conventional thermocouple.
Figure 13B:
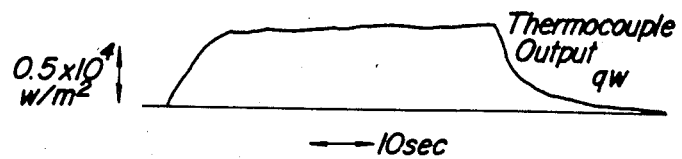

On the other hand, in an apparatus for determining the coefficient $\gamma$, a certain hot air stream is blown onto the heat flux sensor 6, and when the non-steady outputs $\delta_{12}$ and $\delta_{20}$ are stabilized at certain levels, the value of the coefficient $\gamma$ is determined from the thus stabilized output levels by using the previously determined coefficient $\delta$. The value of the heat flux determined by using the heat flux sensor 6 of the invention is checked by a reference value obtained by two thermocouples embedded in the object being measured in the vicinity of the heat flux sensor. The curves of FIGS. 13A and 13B show output levels obtained in the course of determining the coefficient $\gamma$; namely, the heat flux sensor output $(\epsilon_{12}+\epsilon_{20})$ and the heat flux after the calibration as represented by the output from the thermocouple.

The frequency response characteristics and the sensitivity of the heat flux sensor according to the invention will be discussed now. When sinusoidally varying heat input with a non-dimensional angular frequency ω is assumed, the frequency response of the heat flux sensor 6 is approximately as shown in FIG. 4. Here, the non-dimensional angular frequency ω is determined from heat input sinusoidal frequency f, the thickness L of the heat resistive thin film 3, and the heat conductivity α of the heat resistive thin film 3 by the following formula.

$$\omega = 2\pi f L^2 / \alpha$$

Accordingly, the cutoff frequency $f_c$, at which the output level is reduced to $1/\sqrt{2}$ of the value in the flat portion of the frequency response characteristics, is related to the thickness L of the heat resistive thin film 3 as shown by the following equation (8).

$$L = \sqrt{\alpha \cdot \omega_c / 2\pi f_c} \qquad (8)$$

Here, $\omega_c$ is the non-dimensional cutoff angular frequency and equals 2.6.

The maximum sensitivity of the heat flux sensor depends on
(1) the frequency response characteristics of the sensor,
(2) the upper limit of the sensor surface temperature rise, and
(3) the upper limit of temperature rise due to the Joule heat generated by the metallic thin films acting as resistance thermometer elements.

The maximum sensitivity is given by $$\{(e_1 - e_2)/qw\}_{max} = a_1 \cdot (\sqrt{\Delta T_{max}/k}) \cdot (\sqrt{L_{max}}) \cdot m/(m+1) \cdot (\sqrt{A \cdot r}) \qquad (9)$$

Here, $\Delta T_{max}$ is the upper limit of the sensor surface temperature rise, $L_{max}$ is the upper limit of the thickness of the heat resistive thin film, A is the area of the metallic thin films acting as resistance thermometer elements, and γ is the resistivity of the metallic thin film.

The accuracy of the measurement effected by the heat flux sensor of the invention will be discussed now. As can be seen from equation (6), the output of the heat flux sensor 6 is given as the sum of a differential component $\epsilon_{12}$ representing the difference between the resistances of the metallic thin films 4 and 5 on the opposite surfaces of the heat resistive thin film 3 and an in-phase component $\gamma \cdot \epsilon_{20}$ representing the effect of the temperature rise of the sensor 6 itself. The ratio E between the measured quantity (qw/γ) and the in-phase component $\gamma \cdot \epsilon_{20}$ can be defined as follows.

$$E = (\delta \cdot \epsilon_{20})/(qw/\gamma) \qquad (10)$$

In general, if the above ratio E becomes too large due to the temperature rise of the heat flux sensor 6 during the measurement of the heat flux, the measuring error of both the differential and in-phase components $\epsilon_{12}$, $\epsilon_{20}$ causes a digit-drop error with respect to the measured quantity (qw/γ).

Rearrangement of the equation (10) gives the following expression for the above ratio E.

$$E = \frac{a_2 - a_1}{a_1} \cdot \frac{T_2}{T_1 - T_2} \qquad (11)$$

Accordingly, in the heat flux sensor according to the present invention, a high accuracy of measurement can be ensured by selecting similar temperature coefficients $a_1$ and $a_2$ of electric resistance for the two metallic thin films 4 and 5 deposited on the opposite surfaces of the heat resistive thin film 3 as resistance thermometer elements and/or by setting the temperature difference $(T_1 - T_2)$ between the two metallic thin films 4 and 5 as large as possible.

A practical application of the multi-layered heat transfer gauge of the invention will be described next for the case of the measurement of heat transfer at a turbulent flow boundary layer. A flat plate model with a measuring cross-sectional area of 150 mm × 150 mm was placed in a supersonic wind tunnel while providing a cooling means as shown in FIG. 11. Measurement was made under the following conditions.

Figure 14:
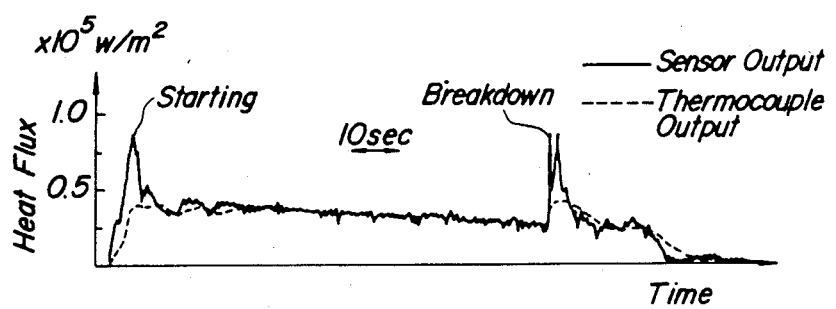
FIG. 14 shows the measured characteristics curve of a multi-layered heat transfer gauge of the invention as compared with the corresponding characteristics curve of a conventional gauge.

Mach number: 3.84
Total pressure: $1.25 \times 10^6$ Pa
Total temperature: 114° C.
Wall temperature to total temperature ratio $T_w/T_o$: 0.77
Reynolds number based on the distance of the measuring point from the leading edge of the flat plate model: $2.06 \times 10^7$ FIG. 14 shows the result of the measurement. The solid line in the figure shows the heat flux as determined by the measurement with the heat flux sensor of the invention, while the dotted line of the figure shows reference values of the heat flux as determined by thermocouples mounted on the top and bottom surfaces of the flat plate model at a sideway distance of 10 mm from the sensor of the invention for the purpose of checking. As can be seen from the comparison of the solid line and the dotted line of the figure, the heat flux sensor of the invention provides the same output as that of the thermocouples in the steady state, and yet the sensor of the invention clearly has much faster response under transient conditions as compared with that of the thermocouples at both the starting and the breakdown of the wind tunnel.

Further, the coefficient of heat-transfer was measured by the heat flux sensor of the invention over the entire range of a so-called shock wave-turbulent boundary layer interaction which was produced by applying an oblique shock wave with a wedge angle of 10.0° to a turbulence boundary layer on a flat plate model placed in a supersonic wind tunnel. The result of the measurement is shown in FIG. 15. The conditions of the measurement were as follows.

Mach number: 4.05
Total pressure: 1.22 MPa
Total temperature: 493° K.
Wall temperature to total temperature ratio $T_w/T_o$: 0.60
Reynolds number based on the distance of the measuring point from the leading edge of the flat plate model: $1.3 \times 10^7$ As can be seen from the characteristics curve of FIG. 15, the heat flux sensor of the invention facilitates clear-cut observation and accurate measurement of the phenomenon that, in the interaction range, the coefficient on a heat-transfer varies greatly in steps of spatially small scale.

The heat flux sensor of the invention used in the above measurements had a spatial resolution of 0.2 mm and a cutoff frequency of the frequency response characteristics of 600 Hz, which spatial resolution and cutoff frequency have been impossible to obtain with the above-mentioned conventional heat flux sensors used in wind tunnels with long flow duration. Further improvement can be expected in the above characteristics of the heat flux sensor of the invention.

As described in the foregoing, a multi-layered heat transfer gauge according to the present invention comprises a heat resistive thin film having a pair of metallic thin films bonded to opposite surfaces thereof in a multi-layered fashion, the metallic thin films acting as resistance thermometer elements, so that the gauge can measure heat flux with a high spatial resolution and can follow rapid change of heat flux with a quick response. Since the measuring principle of the multi-layered heat transfer gauge of the invention is based on steady state temperature gradient in the heat resistive thin film thereof, it has an excellent steady state response characteristics which greatly exceeds that of a conventional thin film heat transfer gauge.

Therefore, as a first feature of the invention, the multi-layered heat transfer gauge of the invention facilitates the measurement of heat flux at a high spatial resolution in a wind tunnel having long flow duration and the measurement of rapid transient change in that flux with a quick response.

As a second feature, the multi-layered heat transfer gauge of the invention simplifies the calibration of gauges of this kind. Conventional thin film heat transfer gauges require complicated electric circuits for calibration, but the measurement of the multi-layered heat transfer gauge of the invention can be calibrated easily with a minimum number of circuits.

As a third feature, the multi-layered heat transfer gauge of the invention is very easy to handle and extremely simple in structure, so that it can be easily mounted on any desired location of an object. With the multi-layered heat transfer gauge of the invention, the level of the heat flux being measured can be determined directly from the measured output of the gauge, which output is in the form an output voltage from a bridge circuit connected with the metallic thin films acting as resistance thermometer elements. On the other hand, with conventional thin film heat transfer gauges, complicated equivalent circuits and/or complicated numerical calculation have been required in order to determine the level of heat flux from the measured output of the gauge. Thus, the invention provides a much simpler means for determining the heat flux as compared with conventional gauges therefor.

Although the invention has been described with a certain degree of particularity, it is understood that the present disclosure has been made only by ways of example and that numerous changes in details of construction and the combination and arrangement of parts may be resorted to without departing from the scope of the invention as hereinafter claimed.

What is claimed is:
1. A multi-layered heat transfer gauge, comprising
a heat resistive thin film having a heat conductivity $\kappa$ and a thickness L between upper and lower opposite surfaces;
a first metallic thin film having a resistance $r_1$ and a temperature coefficient of resistance $a_1$ bonded to the upper surface of said heat resistive thin film and a second metallic thin film having a resistance $r_2$ and a temperature coefficient of resistance $a_2$ bonded to the lower surface of said heat resistive thin film; and
measuring means for measuring the temperature gradient across said heat resistive thin film, said measuring means including
a first resistor $R_1$ connected in series with said first metallic thin film to form a first series circuit;
a second resistor $R_2$ connected in series with said second metallic thin film to form a second series circuit; and
third and fourth resistor $R_S$ and $r_s$ respectively connected in series to form a third series circuit, said first, second and third series circuits being connected in parallel, a voltage V being connected across the parallel connection of said first, second and third series circuits, a voltage $e_1$ being generated at the connection of said first resistor and said first metallic thin film, a voltage $e_2$ being generated at the connection of said second resistor and said second metallic thin film and a voltage $e_0$ being generated at the connection of said third and fourth resistors, whereby the heat flux qw entering said heat resistive thin film is given by the equation:

$$q_w = \gamma(\epsilon_{12} + \delta \cdot \epsilon_{20}),$$

where
$\epsilon_{12} = (e_1 - e_2)V$
$\epsilon_{20} = (e_2 - e_0)/V$
$\delta = (a_2 - a_1)/a_2$; and
$\gamma = (\kappa/L) \cdot (1/a_1) \cdot (m+1)^2/m$, where
$m = R_s/r_s$.

2. A multi-layered heat transfer gauge as set forth in claim 1 which further comprises an electric insulation layer attached to one of the upper and lower surfaces of said heat resistive thin film and to the metallic thin film bonded to said one surface of said heat resistive thin film, and a heat conductive substrate attached to said electric insulation layer, said substrate supporting said heat resistive thin film and said electric insulation layer.

* * * * *